United States Patent
Aytemir et al.

(10) Patent No.: US 9,975,884 B2
(45) Date of Patent: May 22, 2018

(54) KOJIC ACID-DERIVED MANNICH BASES WITH BIOLOGICAL EFFECT

(71) Applicants: Mutlu Aytemir, Ankara (TR); Berrin Ozcelik, Ankara (TR); Ilkay Erdogan Orhan, Ankara (TR); Gulsah Karakaya, Ankara (TR); Fatma Sezer Senol, Ankara (TR)

(72) Inventors: Mutlu Aytemir, Ankara (TR); Berrin Ozcelik, Ankara (TR); Ilkay Erdogan Orhan, Ankara (TR); Gulsah Karakaya, Ankara (TR); Fatma Sezer Senol, Ankara (TR)

( * ) Notice: Subject to any disclaimer, the term of this patent is extended or adjusted under 35 U.S.C. 154(b) by 0 days. days.

(21) Appl. No.: 15/327,105

(22) PCT Filed: May 17, 2016

(86) PCT No.: PCT/TR2016/000070
§ 371 (c)(1),
(2) Date: Jan. 18, 2017

(87) PCT Pub. No.: WO2016/209180
PCT Pub. Date: Dec. 29, 2016

(65) Prior Publication Data
US 2017/0197946 A1 Jul. 13, 2017

(30) Foreign Application Priority Data
Jun. 22, 2015 (TR) ............... a 2015 07653

(51) Int. Cl.
C07D 405/06 (2006.01)
(52) U.S. Cl.
CPC ................. *C07D 405/06* (2013.01)
(58) Field of Classification Search
CPC .................................................. C07D 405/06
See application file for complete search history.

(56) References Cited

PUBLICATIONS

Aytemir et al (2012): Medicinal Chemistry and Drug Design (2012), Prof. Deniz Ekinci (Ed), ISBN: 978-953-51-0513-8.*
Mutla Dilsiz Aytemir, et al ; "Synthesis and anticonvulsant activity of new kojic acid derivatives", Arzneimittelforschung; vol. 60; No. 1, 2010; pp. 22-29; XP002760856.
Database Registry [Online] Chemical Abstracts Service; Columbus, Ohio; US; Aug. 28, 2011 (Aug. 28, 2011); XP002760857; Database accession No. 1324084-63-0 RN 1324084-63-0.
Burdock, G. A., et al., "Evaluation of Health Aspects of Kojic Acid in Food", Regulatory Toxicology and Pharmacology, 2001, vol. 33, pp. 80-101.
Kim, D. H., et al., "Development of 5-[(3-Aminopropyl)phosphinooxy]-2-(hydroxymethyl)-4H-pyran-4-one as a Novel Whitening Agent", Chem. Pharm. Bull, 2003, vol. 51, pp. 113-116.
Brtko, J., et al., "Kojic Acid and its Derivatives: History and Present State of Art", Cent. Eur. J. Publ. Health, 2004, 12 suppl. , pp. S16-S18.
Bentley, R., "From miso, saké and shoyu to cosmetics: a century of science for kojic acid", Nat. Prod. Rep., 2006, vol. 23, pp. 1046-1062.
Uchino, K., et al., "Kojic Acid as an Anti-speck Agent", Agric. Biol. Chem., 1988, vol. 52, No. 10, pp. 2609-2610.
Noh, Jin-Mi, et al. "Kojic Acid—Tripeptide Amide as a New Tyrosinase Inhibitor", PeptideScience, 2007, vol. 88, No. 2, pp. 300-307.
Noh, Jin-Mi, et al., "Kojic acid—amino acid conjugates as tyrosinase inhibitors", Bioorganic & Medicinal Chemistry Letters, 2009, vol. 19, pp. 5586-5589.
Kim, H., et al.. "Solid-phase synthesis of kojic acid-tripeptides and their tyrosinase inhibitory activity, storage stability, and toxicity", Bioorganic & Medicinal Chemistry Letters, 2004, vol. 14, pp. 2843-2846.
Lee, Y. S., et al., "Synthesis of Tyrosinase Inhibitory Kojic Acid Derivative", Arch. Pharm. Chem. Life Sci. 2006, vol. 339, pp. 111-114.
Rho, H. S., et al., "Kojyl thioether derivatives having both tyrosinase inhibitory and anti-inflammatory properties", , Bioorganic & Medicinal Chemistry Letters,, 2010, vol. 20, pp. 6569-6571.
Rho, H. S., et al., "Ester Derivatives of Kojic Acid and Polyphenols Containing Adamantane Moiety with Tyrosinase Inhibitory and Anti-inflammatory Properties", Bull Korean Chem. Soc., 2011, vol. 32, No. 4, pp. 1411-1414.
Kwak, Seon-Yeong, et al., "Enhanced cell permeability of kojic acid—phenylalanine amide with metal complex", Bioorganic & Medicinal Chemistry Letters, 2010, vol. 20, pp. 738-741.
Kasser, J. H., et al., "Mannich products of kojic acid and N-heterocycles and their Ru(II)—arene complexes: Synthesis, characterization and stability", Journal of Organometallic Chemistry, 2010, vol. 695, pp. 875-881.

* cited by examiner

*Primary Examiner* — Golam M Shameem
(74) *Attorney, Agent, or Firm* — Ladas & Parry LLP

(57) ABSTRACT

The present invention relates to kojic acid-derived mannich base compounds with biological effect, and hydrates, solvates, pharmacologically acceptable salts or geometric isomers thereof. Said compounds have antidermatophytic, antimycobacterial, antityrosinase, anti-aging and antioxidant effect.

8 Claims, No Drawings

KOJIC ACID-DERIVED MANNICH BASES WITH BIOLOGICAL EFFECT

RELATED APPLICATION INFORMATION

This application is a 371 of International Application PCT/TR2016/000070 filed 17 May 2016, which claims priority from Turkish Application No: 2015/07653 filed 22 Jun. 2015, the disclosures of which are incorporated in their entirety by reference herein.

FIELD OF THE INVENTION

The present invention relates to the following kojic acid-derived mannich base compounds with biological effect, and hydrates, solvates, pharmacologically acceptable salts or geometric isomers thereof,

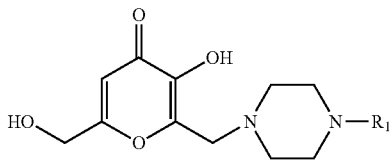

wherein $R_1$ is selected as

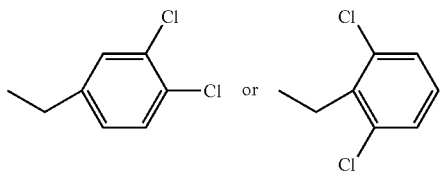

BACKGROUND ART

Nowadays, tyrosinase inhibitors are gradually gaining importance in medicine, cosmetics and food industries. Several natural or synthetic tyrosinase inhibitors have been discovered. However, a few of them can be used as skin bleaching agents due to the toxicity problems. The most important skin bleaching agents are hydroquinone, hydroquinone manomethyl ether, arbutin, kojic acid and azelaic acid. Use of hydroquinone in skin bleacher cosmetics is prohibited because of its clinical side effects, and use of less toxic derivatives thereof is preferred. Only a few antimelanogenic agents such as kojic acid and arbutin are commercially available in the market Kojic acid has antibacterial and antifungal properties, which inhibits catecholase activity of tyrosinase that is an essential rate-limiting enzyme in biosynthesis of melanin pigment which gives skin its color. Therefore, it is contained in dermocosmetics/cosmeceutics for depigmentation after sunburn and in the treatment of hyperpigmentation in the cosmetic industry in order to prevent enzymatic darkening, for its skin bleaching effect. The presence of kojic acid in cosmetic products inhibits tyrosinase enzyme by preventing reuptake of oxygen required for slow and reversible competitive darkening, and it is also known that it forms chelation with active site copper metals, which is effective on the enzyme activity (Chen 1991; Burdock 2001; Kim 2003; Brtko 2004; Bentley 2006). Iron released in the skin due to chronic exposure to the sun rays causes wrinkles. The experiments of kojic acid on hairless rats showed that wrinkles observed on the kojic acid administered rats subjected to UV rays are less than those seen on the skin of the rats not received kojic acid. Furthermore, it is also used in the food and cosmetic industry in order to increase shelf life, due to its protective effect against physical and chemical degradation. In order to prevent spot formation resulting from storage and processing of colored food products, kojic acid also finds application as an anti-spot due to its tyrosinase inhibitory feature (Uchino 1988).

In recent years, in order to improve the low stability of kojic acid, ester, tripeptide-amides and aminoacid-amides are synthesized, and an examination made on the antityrosinase activity thereof revealed that their stability is increased to a great extent. This result is based on an increase in hydrophobic interactions between the synthesized compounds and tyrosinase active site (Noh 2007; Noh 2009; Kim 2003; Kim 2004). In the subsequent studies, metal complexes of these derivatives with strong antityrosinase effect are prepared in order to solve the problem of low cellular permeability (Kwak 2010). In another study, tyrosinase inhibitory activity is examined, wherein kojic acid derivatives are obtained by joining pyrone cores of two kojic acid molecules through an ethylene linkage, which are 8 times more active than kojic acid (Lee 2006). In kojyl thioether derivatives, tyrosinase inhibitory activity is also increased by appropriate lipophilic alkyl chains (Rho 2010), and in ester derivatives, compounds are synthesized which are more effective than the kojic acid (Rho 2011). Moreover, complexes of kojic acid derivatives in the form of mannic base with ruthenium metal are prepared, to obtain anticancer activity (Kasser 2010). Currently, use of kojic acid in pharmaceutical products is not approved by the FDA. In a research on current use concentrations conducted by Personal Care Products Council, it is observed that kojic acid is used at a concentration of 0.1-2%, with the highest concentration being used in face and neck creams, lotions and powders.

An article titled "Synthesis and Evaluation of Anticonvulsant and Antimicrobial Activities of 3-Hydroxy-6-methyl-2-substituted 4W-Pyran-4-one Derivatives" discloses the compounds synthesized from kojic acid, and having the chemical formula given below. Herein, it is determined that a compound, wherein R is a benzyl, does not exhibit anticonvulsant and antifungal activity.

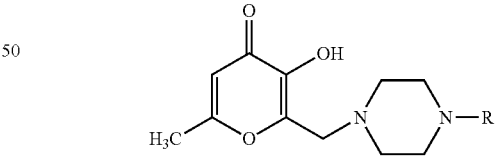

In another study, 3-hydroxy-6-hydroxymethyl-2-substituted 4H-pyran-4-one derivatives are synthesized and their anticonvulsant activity is examined (Aytemir et al., Arzneimittelforschung 2010; 60(1):22-29).

Since kojic acid exhibits high toxicity against ceils and low stability against water and oxygen, it has a limited application area. Furthermore, kojic acid and some derivatives thereof are low soluble in oil and unstable at high temperature for long-term storage. This directly prevents use of those substances in oil-containing cosmetic and skin care products. For kojic acid used as a skin bleacher, skin lightener and depigmentation agent in cosmetic products, ester derivatives such as kojic dipalmitate and kojic isopaimitate are present in the marketed products as a cosmetic ingredient. Therefore, it has become important to obtain more reliable new derivatives of kojic acid, in order to improve physical properties and biological activities thereof and enhance its industrial application area. Moreover, kojic acid that is allowed to be used at only low doses due to its toxic effects on thyroid gland has low permeability and stability problems. Therefore, more efficacious and safe products should be developed. Due to their damage on both medical and leather and textile sectors, dermatophytes are fungi that cause great economical damages. Today, there is a need for new antifungal agents since antifungal drugs are used in the treatment of dermatophytes that settle on skin, hair and nails where they cause common infections, and fungi rapidly develop resistance to existing drugs. *Mycobacterium avium* subsp. *paratubervuiosis* is a pathogen which causes paratuberculosis in milk cows, i.e. Johne disease, and which is also linked to Crohn disease in humans. It is abundant in nature, soil and water. It is also commonly available in household dust and plants. *Mycobacterium avium* complex (MAC) is the cause of pulmonary diseases in AIDS patients. It is a disease cause in animals and humans, it is a factor responsible for contamination of water. It is spread by ingestion of contaminated water and foods. New treatment methods have been developed by preparing combinations of commercially available antibiotics, but new antibiotics could not be developed which have antimycobacterial effect.

BRIEF DESCRIPTION OF THE INVENTION

The present invention relates to the following kojic acid-derived mannich base compounds with biological effect, and geometric isomers or pharmacologically acceptable salts thereof,

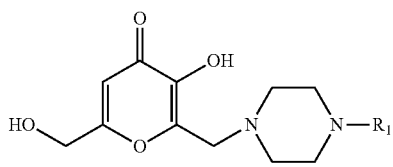

wherein $R_1$ is

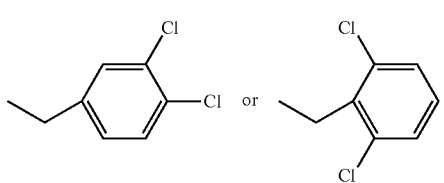

The inventive compounds have antidermatophytic, antimycobacterial, antityrosinase, anti-aging and antioxidant effects.

OBJECT OF THE INVENTION

An object of the present invention is to synthesize new kojic acid-derived compounds, which have a better permeability than kojic acid and are not irritative, in high amounts and without by-product formation by means of a simple method that is conducted at room temperature and is efficient.

Another object of the present invention is to synthesize compounds that exhibit better antityrosinase, antioxidant, anti-aging, antidermatophytic and antimycobacterial effect than other kojic acid and derivative compounds.

DESCRIPTION OF THE INVENTION

The invention consists of two new bioactive compounds in the form of a mannich base synthesized from kojic acid. Physical properties of the compounds such as efficiency of synthesis reactions and melting points are determined. The structure of the compounds are demonstrated by spectroscopic methods such as IR, $^1$H-NMR, $^{13}$C-NMR and ESI-MS, and proved by elemental analysis results. Antidermatophytic activity of the compounds against *Trichophyton mentagrophytes* var. *erinacei*, *Epidermophyton floccosum* and *Microsporum gypseum* as well as their antimycobacterial activity against *Mycobacterium tuberculosis* H37Rv (ATCC 27294) and *M. avium* (ATCC 15769) are analyzed under non-toxic concentrations using MRC-5 and He-La cell lines. Antityrosinase activity thereof is determined by spectrophotometric method using L-DOPA as a substrate. Antioxidant activity is determined by the methods of 2,2-diphenyl-1-picrilhydrasil (DPPH), N,N-dimethyl-p-phenylenediamine (DMPD) radical scavenging activity, metal chelation effect, iron-(FRAP), phosphomolybdenum-(PRAP) reducing antioxidant power. Elastase and collagenase enzyme inhibitions are performed to determine anti-aging activity. Due to their antityrosinase, antioxidant, anti-aging, antidermatophytic and antimycobacterial effects, the compounds may be used in medicine, cosmeceutical, food and textile industry.

In order to obtain compounds having a higher antityrosinase activity than kojic acid, the compounds of Formula 1 and 2 of the present invention have been synthesized which have a similar structure to kojic acid but is more lipophilic and alkaline through a benzylpiperazine group added to the structure with mannich base.

Formula 1

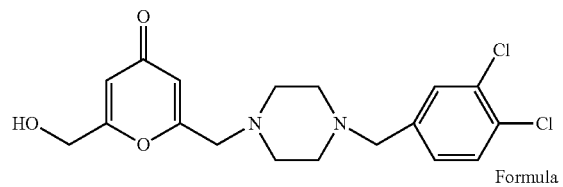

Formula 2

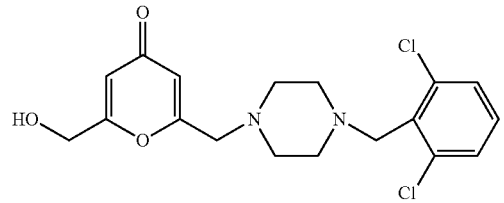

By increasing oil solubility of the obtained compounds, low permeability problem of the kojic acid is eliminated. Synthesis is performed with a simple method which is conducted at room temperature and is efficient. No by-products are generated. This method is advantageous in synthesis of a high amount of substance, with its high productivity and simplicity.

Synthesis of 3-Hydroxy-6-hydroxymethyl-2-substituted-4H-pyran-4-one derivatives

Formaldehyde is added to substituted benzylpiperazine derivative (1 mol) and is mixed. Kojic acid {1 mol} is added to the solution. An amount of methanol sufficient to dissolve kojic acid is added to the medium and shaken at room temperature. Precipitated solid is filtered under vacuum and rinsed with cold methanol.

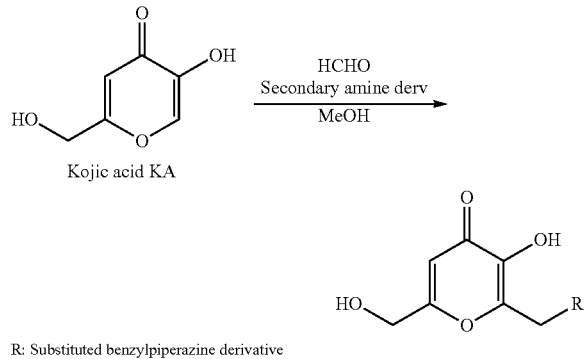

R: Substituted benzylpiperazine derivative

3-Hydmxy-6-(hydmxymethyl)-2-[[4-(3,4-diclombenzyl)piperazine-1il]methyl-4H-pyran-4-one presented in Formula 1 and synthesis Kojic acid is obtained from 1-(3,4-diclorobenzyl)piperazine and formaldehyde using genera) synthesis method. Melting point: 180-1<*>C, Yield: 90%. White powder crystals. Insoluble in water, low-solubility in methanol, ethanol and acetone, and soluble in chloroform.

IR spectrum; peaks at 1607 (C=O, stretching), 1455 (C=C, stretching), 1196 cm$^{-1}$ (C—O, stretching). $^1$H-NMR spectrum; peaks at δ (DMSO-d$_6$, 400 MHz) 2.37 (4H; brs; piperazine), 2.47 (4H; brs; piperazine). 3.45 (2H; s; —CH$_2$—), 3.51 (2H; s; —CH$_2$-phenyl), 4.28 (2H; s; —CH$_2$OH), 5.61 (1H; brs; —CH$_2$OH); 6.31 (1H; s; H$^6$), 7.28 (1H; dd; J=8; J=2; Ar—H$^{6'}$), 7.51 (1H; d; J=2; Ar—H$^2$), 7.56 (1H; d; J=8; Ar—H$^{5'}$) 8.89-8.98 (1H; br; —OH). $^{13}$C NMR spectrum; peaks at δ (DMSO, 400 MHz) 52.27 (—CH$_2$), 52.32 (—CH$_2$), 53.46 (—CH$_2$), 59.51 (—CH$_2$), 60.24 (—CH$_2$), 108.85 (—CH), 128.84 (—CH), 129.24 (—CH), 130.24 (—CH), 130.33 (—C$_{phenyl}$), 130.74 (—C$_{phenyl}$), 139.56 (—C$_{phenyl}$), 143.59 (—C$_{pyrone}$), 146.41 (—C$_{pyrone}$). 167.49 (—C$_{pyrone}$), 173.49 (—C$_{pyrone}$). On mass spectrum (ESI-MS) m/z; peaks are seen at 399 (100%, M$^+$), 401 (M$^+$+2), 421 (M*+Na).

| Analysis: $C_{18}H_{20}Cl_2N_2O_4$ (MA: 399.27 g/mol) | | | |
|---|---|---|---|
| | C % | H % | N % |
| Calculated: | 54.15 | 5.05 | 7.02 |
| Found: | 54.01 | 5.10 | 7.27 |

3-Hydmxy-6-(hydmxymethyl)-2-[{4-(2,6 diclorobenzyl)piperazme-1-il]methyl-4H-pyran-4-one presented in Formula 2 and synthesis Kojic acid is obtained from 1-(2,6-diclorobenzyl)piperazine and formaldehyde using general synthesis method. Melting point 196-7° C., Yield: 93%. White powder crystals. Insoluble in water, methanol, ethanol and acetone, but soluble in chloroform.

IR spectrum; peaks at 1607 (C=O, stretching), 1435 (C=C, stretching), 1,197 cm$^{-1}$ (C—O, stretching). $^1$H-NMR spectrum; peaks at δ (DMSO-d$_6$, 400 MHz) 2.41 (4H; brs; piperazine), 2.49 (4H; brs; piperazine), 3.50 (2H; s; —CH$_2$—), 3.66 (2H; s; —CH$_2$-fenil), 4.28 (2H; s; —CH$_2$OH), 5.60 (1H; brs; —CH$_2$OH); 6.30 (1H; s; H$^6$), 7.31 (1H; t; J=8; J=2; Ar—H$^{4'}$), 7.44 (2H; d; J=8; Ar—H$^{3'}$, H$^{5'}$), 8.89-8.98 (1H; br; —OH). $^{13}$C-NMR spectrum; peaks at δ (DMSO, 400 MHz) 52.28 (—CH$_2$), 52.41 (—CH$_2$), 53.43 (—CH$_2$), 55.79 (—CH$_2$), 59.49 (—CH$_2$), 108.84 (—CH), 128.48 (—CH), 129.73 (—CH), 133.54 (—C$_{phenyl}$), 135.99 (—C$_{phenyl}$), 143.58 (—C$_{pyrone}$), 146.36 (—C$_{pyrone}$), 167.48 (—C$_{pyrone}$), 173.46 (—C$_{pyrone}$). On mass spectrum (ESI-MS) m/z; peaks are seen at 399 (100%, M$^+$), 401 (M$^+$+2), 421 (M$^+$+Na).

| Analysis: $C_{18}H_{20}Cl_2N_2O_4$ (M.A.: 399.27 g/mol) | | | |
|---|---|---|---|
| | C % | H % | N % |
| Calculated: | 54.15 | 5.05 | 7.02 |
| Found: | 54.04 | 4.87 | 7.35 |

In order to determine the activity of the compounds according to the present invention, the claimed compounds are compared with kojic acid and different kojic acid derivatives and tested.

It is found that the compound of Formula 1 has a greater tyrosinase inhibitory effect at low doses than kojic acid (Table 1).

TABLE 1

| Low-dose antityrosinase activity results | | | | | | | |
|---|---|---|---|---|---|---|---|
| | 0.0025 mg/ml | 0.005 mg/ml | 0.01 mg/ml | 0.025 mg/ml | 0.05 mg/ml | 0.1 mg/ml | 0.25 mg/ml |
| Compound of Formula 1 | 23.63 ± 1.65 | 37.81 ± 0.54 | 51.25 ± 1.09 | 56.79 ± 0.44 | 70.62 ± 1.62 | 73.57 ± 4.81 | 80.63 ± 2.01 |
| Kojic Acid | | | | 18.65 ± 1.33 | 44.74 ± 0.53 | 61.28 ± 2.03 | 77.44 ± 0.68 |

Tyrosinase inhibitory activity results of a group of kojic acid-derived compounds, a compound of Formula 1 and a compound of Formula 2 of the present invention and kojic acid are analyzed (Tables 1 and 2). The values of the compound of Formula 1 and kojic acid IC50 (mg/ml) are 0.011±0.001 mg/ml and 0.067±0.001 mg/ml, respectively. It is determined that the compound of Formula 1 has a 6 times higher antityrosinase effect than kojic acid. It is also determined that the compound of Formula 2 exhibits medium inhibition (43.74±2.72 mg/ml) at the highest dose (5 mg/ml).

TABLE 2

Antityrosine activity results

| —$R_1$ | —$R_2$ | Tyrosinase Enzyme Inhibition (Inhibition % ± S.S) | | | | |
|---|---|---|---|---|---|---|
| | | 0.5 mg/ml | 1 mg/ml | 2.5 mg/ml | 5 mg/ml | IC50 (mg/ml) |
| —$CH_3$ | 4-Cl-phenyl | 28.33 ± 1.83 | 27.69 ± 0.92 | 25.66 ± 2.44 | — | |
| —$CH_2Cl$ | 2,6-dichloro-ethylphenyl | 14.27 ± 1.80 | 18.88 ± 1.61 | 19.00 ± 3.40 | 22.60 ± 3.88 | |
| —$CH_2OH$ | 2-Cl-phenyl | 10.37 ± 0.68 | 24.71 ± 2.31 | 22.40 ± 0.14 | 14.52 ± 0.41 | |
| —$CH_2OH$ | 3-Cl-phenyl | 25.40 ± 0.89 | 28.64 ± 0.13 | — | — | |

| —$R_1$ | —$R_2$ | Microorganisms | | | | | | |
|---|---|---|---|---|---|---|---|---|
| | | Trichophyton mentagrophytes var. erinacei | | Epidermophyton floccosum | | Microsporum gypseum | | Mycobacteria |
| | | NCPF 375 | Isolated strains | RSKK 3027 | Isolated strains | NCPF 580 | Isolated strains | M. tuberculosis ATCC-27294 | M. avium ATCC-15769 |
| | | MIC | | MIC | | MIC | | MIC | |
| —$CH_3$ | 4-Cl-phenyl | 4 | 16 | 16 | 32 | 16 | 32 | 64 | 16 |
| —$CH_2Cl$ | 2,4-dichloro-ethylphenyl | 4 | 8 | 4 | 8 | 4 | 8 | 16 | 8 |

TABLE 2-continued

Antityrosine activity results

| R1 | R2 | | | | | | | | |
|---|---|---|---|---|---|---|---|---|---|
| —CH₂Cl | 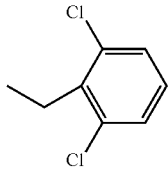 2,6-dichloro-ethylphenyl | 4 | 8 | 4 | 8 | 4 | 8 | 16 | 8 |
| —CH₂OH | 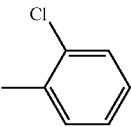 2-chloro-methylphenyl | 4 | 8 | 8 | 8 | 4 | 8 | 32 | 16 |
| —CH₂OH | 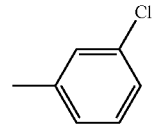 3-chloro-methylphenyl | 4 | 8 | 4 | 8 | 4 | 8 | 32 | 16 |
| —CH₂OH (Compound of Formula 1) | 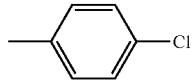 4-chloro-methylphenyl | 2 | 4 | 2 | 4 | 2 | 4 | 16 | 16 |
| —CH₂OH (Compound of Formula 2) | 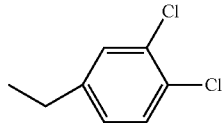 3,4-dichloro-ethylphenyl | 1 | 2 | 2 | 2 | 2 | 2 | 16 | 2 |
| —CH₂OH | 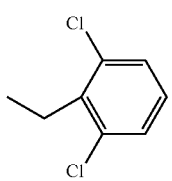 2,6-dichloro-ethylphenyl | 1 | 2 | 1 | 2 | 1 | 2 | 32 | 2 |
| Kojic Acid | | 4 | 4 | 4 | 4 | 2 | 2 | 32 | 16 |
| Terbinafine | | 0.125 | 0.25 | 0.25 | 0.5 | 0.25 | 0.5 | — | — |
| Griseofulvin | | 0.5 | 1 | 0.5 | 1 | 0.5 | 1 | — | — |
| Itraconazole | | 0.25 | 0.5 | 0.125 | 0.25 | 0.125 | 0.25 | — | — |
| Isoniazide | | — | — | — | — | — | — | 0.125 | 0.125 |
| Ethambutol | | — | — | — | — | — | — | 2 | 32 |
| Streptomycin | | — | — | — | — | — | — | 1 | 32 |

As an antimycobacterial, both compounds have a high activity against *M. avium* at MIC 2 μg ml$^{-1}$ as compared to kojic acid (MIC 16 μg ml$^{-1}$). It is as effective as the reference drug ethambutol and streptomycin (MIC 2 μg ml$^{-1}$) which are still used and available in Turkey (Table 3). A gradual increase in the number of pathogen bacteria and fungus resistant to general therapeutic agents is a current problem around the world. It has become highly important to develop new antibiotics.

Antioxidant activity of the compound of Formula 1, the compound of Formula 2 and kojic acid is determined by the methods of 2,2-diphenyl-1-picrilhydrasil (DPPH), N,N-dimethyl-p-phenylenediamine (DMPD) radical scavenging activity, metal chelation effect, iron-(FRAP), phosphomolybdenum-(PRAP) reducing antioxidant power. An examination of the results of these methods revealed that the compound in Formula 1 (67.57±1.30 μg/ml) and the compound in Formula 2 (58.17±0.99 μg/ml) at a dose amount of 1000 μg/ml has a mild iron chelation effect higher than kojic acid (8.89±0.75 μg/ml) but lower than the reference compound ethylenediaminetetraacetic acid (EDTA, 97.66±0.12-2000 μg/ml). Since iron ion and other transition metal ions catalyze oxidation in the body, it is important to examine metal chelation effect of an antioxidant. A comparison of antioxidant power of phosphomolybdenum structure and antioxidant effects demonstrates that the compound of Formula 2 (0.187±0.017 μg/ml) and the compound of Formula 1 (0.154±0.004 μg/ml), though lower than the reference compound flavonoid quercetin of vegetable origin (0.320±0.005 μg/ml), shows a higher antioxidant effect than kojic acid (0.103±0.006 μg/ml) (Table 4).

TABLE 4

Antioxidant and anti-aging activity results

| | DPPH Free Radical Scavenging Effect (Scavenging % ± S.S) 1000 μg/ml | Metal Chelation Effect (Chelation % ± S.S) 1000 μg/ml | Iron Reduction Antioxidant Power (Absorbance at 700 nm ± S.S) 1000 μg/ml | Phosphomolybdenum Reduction Antioxidant Power (Absorbance at 600 nm ± S.S) 1000 μg/ml | DMPD Radical Scavenging Effect (Scavenging % ± S.S) 1000 μg/ml | Collagenase Enzyme Inhibition (Inhibition % ± S.S) 1000 μg/ml- Stock |
|---|---|---|---|---|---|---|
| Compound of Formula 1 | 14.59 ± 2.52 | 67.57 ± 1.30 | 0.274 ± 0.003 | 0.154 ± 0.004 | 36.05 ± 3.11 | 15.57 ± 2.24 |
| Compound of Formula 2 | 12.20 ± 1.72 | 58.17 ± 0.99 | 0.217 ± 0.002 | 0.187 ± 0.017 | 24.94 ± 1.64 | 12.40 ± 4.57 |
| Kojic Acid | 22.51 ± 2.65 | 8.89 ± 0.75 | 0.757 ± 0.026 | 0.103 ± 0.006 | 41.86 ± 1.10 | 15.18 ± 5.92 |
| Quercetin | 91.14 ± 0.65 | — | 2.015 ± 0.032 | 0.320 ± 0.005 | — | |
| EDTA- 2000 μg/ml | — | 97.66 ± 0.12 | — | — | — | |
| Ascorbic acid | — | — | — | — | 69.58 ± 0.71 | |
| EGCG-15 mM | | | | | | 44.64 ± 2.87 |

Furthermore, elastase and collagenase enzyme inhibition of the compounds of Formula 1 and Formula 2 and kojic acid is tested. No elastase enzyme inhibition is detected in the screened samples whereas a low collagenase enzyme inhibition is detected as compared to the reference compound epigallocatechin gallate (EGCG, 44.64±2.87 μg/ml. However, the compound of Formula 1 (15.57±2.24 μg/ml) showed a higher enzyme inhibition than the compound of Formula 2 (12.40±4.57 μg/ml) and as high as kojic acid (15.18±5.92 μg/ml) (Table 4).

In the experiments performed using cell lines of normal cell MRC-5 and cancer cell He-La, it is seen that the two compounds are effective at a non-toxic dose of 128 μg ml$^{-1}$.

The compound of Formula 1 has a high antimycobacterial, antidermatophytic and antityrosinase feature as well as antioxidant and antiaging activities. It may be used both in preventive and hyperpigmentation treatment as a depigmentation agent, skin bleacher, skin lightener, acne spot remover and wrinkle remover, for its high dermotophytic effect. In cosmetics field, hand and face cream as well as soap preparations may be prepared.

Due to the liphophilic characteristic of the cosmetic products to be prepared with the compound of Formula 1, it is better absorbed by the skin. Thanks to these effects, it will be superior to the products that contain kojic acid and available in the market. As a new antibiotic candidate in medicine, further investigations may be made in pharmaceutics field. It may be used in pharmaceutical, cosmeceutical, food and textile industry, for the activities it exhibits. In food industry, it may be used as an additive to prevent degradation, rancidity and darkening that may occur in fruits and vegetables so as to prevent any damages in production, storage, transportation and marketing processes.

The compound in Formula 2 may be used in medicine, pharmaceutical, cosmeceutical, food and textile industry, due to its high antimycobacterial and antidermatophytic characteristic and mild antityrosinase and antioxidant effect. It may be used in food and textile industries as a protective powder, and in medicine and cosmetic preparations as a cream, lotion, gel or soap formulation for aerosol and topical application. In the treatment of patients with immune system suppression (patients with AIDS, cancer etc.), protective products may be prepared from the compound of Formula 2 by preparing a impregnated mask or spraying on the surface in contact with the solution pharmaceutical products and to air.

The invention claimed is:

1. A compound of the following formula

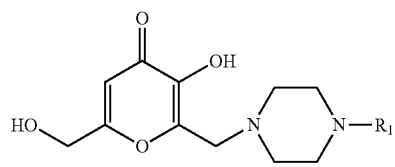

wherein $R_1$ is

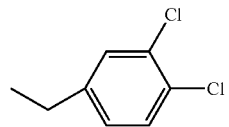

or a hydrate, solvate, pharmaceutically acceptable salt or geometric isomer thereof.

2. A compound according to claim 1, wherein the said compound is
3-Hydroxy-6-(hydroxymethyl)-2[[4-(3,4-dichlorobenzyl) piperazine-1-il]methyl]-4H-pyran-4-one.

3. A compound according to claim 2, having antityrosinase activity.

4. A compound according to claim 2, having antimycobacterial activity.

5. A compound according to claim 2, having antidermatophytic activity.

6. A compound according to claim 2, having antioxidant activity.

7. A compound according to claim 2, having anti-aging activity.

8. A composition for pharmaceutical, cosmeceutical and food and textile materials comprising a compound according to claim 1 as an additive ingredient and at least one excipient.

* * * * *